United States Patent [19]

Takagi

[11] 4,374,763

[45] Feb. 22, 1983

[54] METHOD FOR PRODUCING GAMMA-GLOBULIN FOR USE IN INTRAVENOUS ADMINISTRATION AND METHOD FOR PRODUCING A PHARMACEUTICAL PREPARATION THEREOF

[75] Inventor: Takashi Takagi, Shiga, Japan

[73] Assignee: Morishita Pharmaceutical Co., Ltd., Osaka, Japan

[21] Appl. No.: 181,972

[22] Filed: Aug. 28, 1980

[30] Foreign Application Priority Data

Sep. 17, 1979 [JP] Japan .................................. 54-120357
Jul. 30, 1980 [JP] Japan .................................. 55-105618

[51] Int. Cl.³ ................................................ C07G 7/00
[52] U.S. Cl. ................................. 260/112 B; 424/101; 424/176; 424/177
[58] Field of Search ..................... 260/112 B; 424/101, 424/176, 177

[56] References Cited

U.S. PATENT DOCUMENTS

| | | | |
|---|---|---|---|
| 3,903,262 | 9/1975 | Pappenhagen et al. | 260/112 B X |
| 4,082,734 | 4/1978 | Stephan | 260/112 B |
| 4,093,606 | 6/1978 | Coval | 260/112 B |
| 4,124,576 | 11/1978 | Coval | 260/112 B |
| 4,126,605 | 11/1978 | Schneider et al. | 260/112 B |
| 4,136,094 | 1/1979 | Condie | 260/112 B X |
| 4,154,819 | 5/1979 | Stephan | 260/112 B X |
| 4,160,763 | 7/1979 | Müller | 260/112 B |
| 4,168,303 | 9/1979 | Nishida et al. | 260/112 B |
| 4,276,283 | 6/1981 | Eibl et al. | 260/112 B |

OTHER PUBLICATIONS

Vox: Sang 31: pp. 141–151, (1976), by W. Schneider et al.
Scand. J. Infect Dis. 4; 53–56, (1972), M. Stefansson et al.
Acta Chemica Scandinavica 22, (1968), pp. 490–496.
Acta Chemica Scandinavica 24, (1970), pp. 1585–1589.

*Primary Examiner*—Howard E. Schain
*Attorney, Agent, or Firm*—Wegner & Bretschneider

[57] ABSTRACT

A method for producing gamma-globulin in its native state derived from human sources and suitable for use in intravenous administration and having an anti-complementary activity of lower than 20% ($C'H_{50}v$) is disclosed, in which raw human gamma globulin is brought into suspension in an aqueous solution of a monosaccharide, disaccharide or sugar alcohol, adjusted to a pH value of 7.0 to 9.0 and then subjected to fractional precipitation by adding dextran thereto. The fractions showing anti-complementary activity are removed as precipitates.

1 Claim, 1 Drawing Figure

METHOD FOR PRODUCING GAMMA-GLOBULIN FOR USE IN INTRAVENOUS ADMINISTRATION AND METHOD FOR PRODUCING A PHARMACEUTICAL PREPARATION THEREOF

TECHNICAL FIELD OF THE INVENTION

The present invention relates to the method for producing a gamma-globulin retaining its native state as derived from human source and suitable for use in intravenous administration, and to the method for producing a pharmaceutical preparation based on the gamma-globulin.

BACKGROUND OF THE INVENTION

As a method for separating and collecting gamma-globulin from human blood, the method of Cohn, et al. has been habitually utilized (refer to Cohn, E. J., et al., J. Am. Chem. Soc., 68, 459–475 (1946) and ibid., 72, 465–474 (1950)). However, since the gamma-globulin obtained by the Cohn, et al. contains impurities which show a high anticomplementary activity, its use has been confined only to intramuscular injection. Even in the case of intramuscular injection, the above-mentioned gamma-globulin gives a topical pain, and moreover, since the gamma-globulin remains at the site of injection for a long time, satisfactorily high levels of gamma-globulin in the object's blood are not attainable due to the degradation of gamma-globulin during the long retention at the site of injection. Accordingly, in order to improve such a defect, a method for obtaining gamma-globulin for use safely in intravenous administration, for instance, methods of treating gamma-globulin with an enzyme and an acid, respectively and a method of chemically modifying gamma-globulin, has been devised.

However, owing to the several defects caused by these treatments such as the reduction of half-life of gamma-globulin and the problem of new antigenicity caused by these treatments, the production of a gamma-globulin with its original and native form as derived from human blood has attracted the attention.

As such a method, for instance, a method of using a copolymer of ethylene oxide and propylene glycol (Japanese Patent Application Laying Open No. 81519/74), a method of using hydroxyethylstarch and polyethylene glycol (Japanese Pat. No. 12001/80), a method of using polyethylene glycol (U.S. Pat. No. 4,165,370 and U.S. Pat. No. 4,124,576), etc. have been known.

Since it is very difficult to remove the high polymeric substance which has been once used to remove the impurities from the gamma-globulin and has remained together with the purified gamma-globulin, the high polymeric substance used in the process of the treatment of gamma-globulin is preferably removable completely from the purified gamma-globulin or is preferably administrable intravenously. However, the high polymeric substance which is in used according to the publicly known methods does not necessarily satisfy the above-mentioned conditions.

Further, the gamma-globulin purified by the above-mentioned method, in the case where it is formulated to be a pharmaceutical preparation by the usual method, shows its raised anticomplementary activity again. Accordingly, it is necessary to device a stabilizing method which inhibits the raise of the anticomplementary activity. As a method for stabilizing the purified gamma-globulin, a method of adding an amino acid, a sugar, a neutral salt or a high polymeric non-ionic surfactant of molecular weight of 2,000 to 20,000 at a relatively high concentration to gamma-globulin (Japanese Patent Applications Laying Open Nos. 47515/78 and 20124/79) and a method of adding a neutral salt such as sodium chloride and human serum albumin to gamma-globulin (Japanese Patent Application Laying Open No. 23115/79) are known. In the former case, owing to the high concentration of the stabilizing agent, the formulated preparation results in hypertonic, and in addition, among such additives there are substances not preferable for living bodies. On the other hand, in the latter case, even if the thus obtained purified gamma-globulin has almost no fear of causing transmission of serum hepatitis, however, human serum albumin is highly dangerous in causing such a disease, and the use of such a dangerous stabilizing agent should be avoided. The stability of the added human serum albumin itself also becomes a problem.

DETAILED DESCRIPTION OF THE INVENTION

Figure 1:
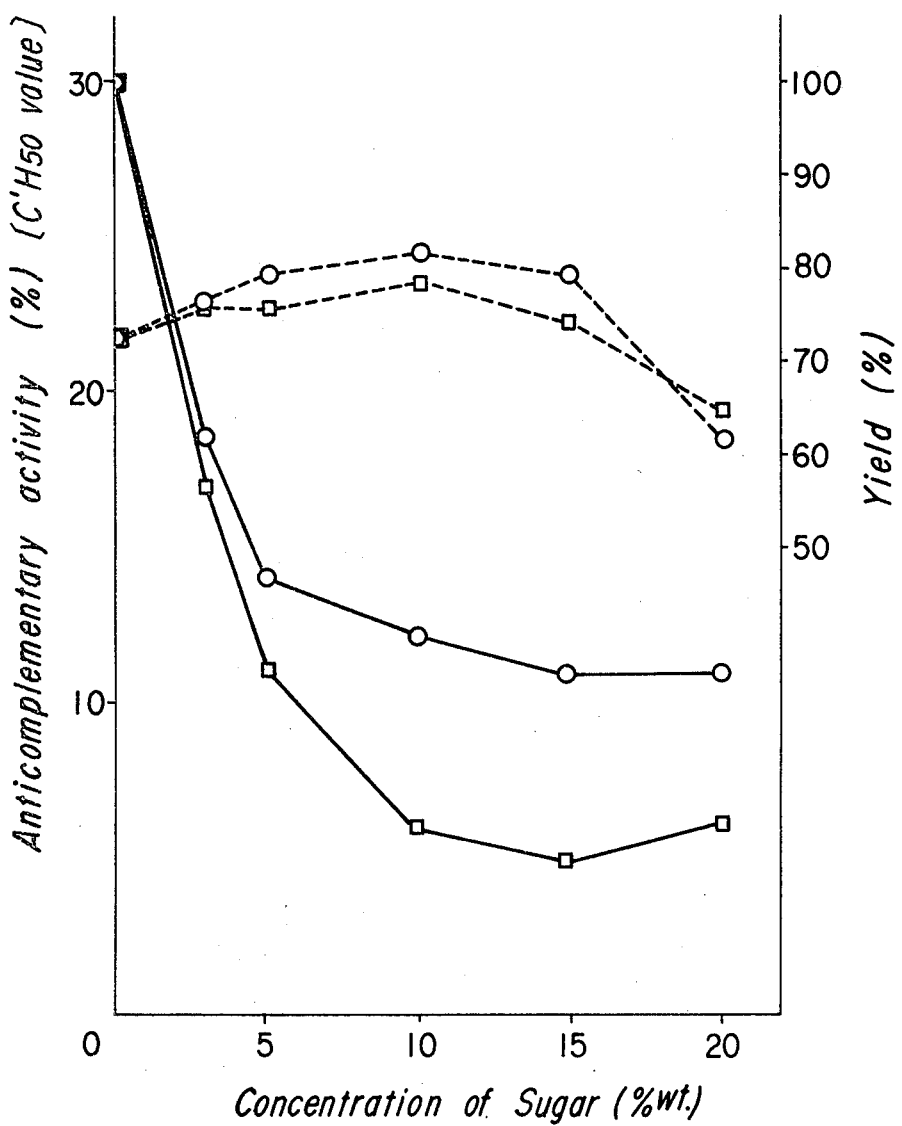
FIG. 1 shows the relationships (1) between the yield of gamma-globulin and the concentration of a sugar such as glucose and mannitol, and (2) between the anticomplementary activity of gamma-globulin and the concentration of the sugar such as glucose and mannitol, both of which were obtained by the same procedure as in example 5, except for adjusting the pH of the suspension to 7.7 wherein white circles indicate the level of glucose, and white squares indicate the level of mannitol, the solid line showing the anticomplementary activity and the dotted line showing the yield of gamma-globulin.

The present invention has one of its specific features of using dextran, which has been hitherto utilized as an injection for human, as the high polymeric substance for removing the impurities which show the anticomplementary activity and, moreover, of the combined use of monosaccharide, disaccharide or sugar alcohol in the above-mentioned case. The anticomplementary activity of the thus obtained gamma-globulin is very low and fully satisfies the standard (the national standard of biological pharmaceutical preparations established by the Ministry of Welfare, the Japanese Government) which requires the anticomplementary activity of less than 20% ($C'H_{50}$ value) at a concentration of the preparation of 50 mg/ml. The yield of the purified gamma-globulin depends on both of the kinds of monosaccharide, disaccharide or sugar alcohol used, and of the conditions of fractionation, however, it is in the range of 74 to 93% of the analytically available amount of gamma-globulin, and accordingly, the method according to the present invention can be highly evaluated as a practical method.

Furthermore, as a result of continued studies for obtaining a stabilizing agent which effectively inhibits the raise of the anticomplementary activity of the pharmaceutical preparation after the production of the preparation based on the thus produced gamma-globulin at a concentration at which the solution shows an osmotic pressure close to the physiological osmotic pressure and is harmless to living bodies, the inventors of the present invention have found that L-arginine, L-lysine or one of their salts is specifically effective in stabilizing gamma-globulin at a concentration of 0.15 to 0.3 mol/liter. The use of such a stabilizer in the process of producing a pharmaceutical preparation of gamma-globulin is the another characteristic feature of the present invention.

The followings are the explanation of the practical method of the present invention:

A raw material for gamma-globulin, represented by Cohn's Fraction II (loc. cit.) is brought into suspension in an aqueous solution of 3 to 15% by weight of monosaccharide such as glucose, fructose, galactose, etc., disaccharide such as lactose, maltose, etc., or sugar alcohol such as mannitol, xylitol, glycerol, etc. at a rate of 25 to 60 ml/g, preferably 45 to 55 ml/g of the protein contained in the fraction, and the pH value of the aqueous suspension is adjusted to 7.0 to 9.0.

Then, the thus prepared aqueous suspension is subjected to fractional precipitation by adding dextran thereinto to 2 to 10% wt./vol., or by adding dextran devidedly in three stages, that is, to 2% wt./vol. at first, then to 3 to 5% wt./vol. and to 6 to 10% wt./vol. at last. The impurities showing the anticomplementary activity are removed during the course of the fractional precipitation as precipitates. The procedures to this point may be practised at room temperature. As the final procedure, ammonium sulfate is added to the mother liquid to 15 to 35% wt./vol. at a temperature of 0° to 10° C., preferably 0° to 5° C. to precipitate the thus purified gamma-globulin suitable for use in intravenous administration.

Although a purified gamma-globulin is obtainable by using solely dextran without using monosaccharide, disaccharide or sugar alcohol at nearly the same yield, the anticomplementary activity is, in this case, 25 to 30 ($C'H_{50}$) at a concentration of gamma-globulin of 50 mg/ml, that is, the product satisfying the standard for biological preparations for pharmaceutical use of less than 20 ($C'H_{50}$) of anticomplementary activity cannot be obtained by this method.

In short, a satisfactory product cannot be obtained by the sole use of dextran but can be obtainable at the first time when monosaccharide, disaccharide or sugar alcohol is further added resulting in the remarkable reduction of the anticomplementary activity. In addition, in the case where monosaccharide, disaccharide or sugar alcohol is singly used, no reduction of the anticomplementary activity is observed, and in the case where hydroxyethyl starch is used instead of dextran, the aqueous solution becomes turbid and it is not able to purify a gamma-globulin.

The pH of the solution in the fractional precipitation is preferably 7.0 to 9.0, and in the cases where the pH is lower than 7.0 or higher than 9.0, the removal of the impurities is insufficient and the anticomplementary activity is not sufficiently reduced. As the dextran for use in this step, Dextran 10 (with an average molecular weight of 10,000), Dextran 40 (with an average molecular weight of 40,000) and Dextran 70 (with an average molecular weight of 70,000) are mentioned, and among them, Dextran 40 is preferably utilized at a concentration of 2 to 10% wt./vol. in connection to the relationship between the anticomplementary activity and the yield of the product.

In the next place where the thus obtained gamma-globulin with a satisfactorily low anticomplementary activity is subjected to production of a preparation for pharmaceutical use, the gamma-globulin is dissolved into an aqueous physiological saline solution at a concentration of 5 to 15% wt./vol., and L-arginine, L-lysine or one of their salts is added to the solution at a concnetration of 0.15 to 0.3 mol/liter and then the pH of the mixture is adjusted to 6.4 to 7.2. It is sterilized by filtering and then freeze-dried to be obtained the product.

The kinds, the concentration in use, and the effectiveness of the stabilizing agents have been elucidated by Examples 1 to 3.

In addition, it has been found that the method according to the present invention for stabilizing the pharmaceutical preparation of gamma-globulin of sufficiently low anticomplementary activity prepared by the method according to the present invention is also applicable in the case where a gamma-globulin prepared by the other method than the method of the present invention is processed to be a pharmaceutical preparation, and that the method gives the pharmaceutical preparation as stabile as the above-mentioned pharmaceutical preparation according to the methods of the present invention. Example 4 shows this situation.

The following Examples exemplify the most preferable modes of operation for practicing the present invention.

EXAMPLE 1

Into each 20 ml of an aqueous physiological saline solution, one gram of the gamma-globulin, obtained by the abovementioned method, having a low anticomplementary activity was dissolved, and glycin, L-alanine, L-arginine, L-arginine hydrochloride, L-lysine, L-lysine hydrochloride, L-ornithine hydrochloride, sodium L-aspartate, sodium L-glutamate and epsilon-aminocaproic acid were respectively dissolved into each solution to a concentration of 0.2 mol/liter.

These mixtures were respectively adjusted by an aqueous 1 N solution of sodium hydroxide or hydrogen chloride to be 7.0 in pH and then were freeze dried. After one hour of the completion of freeze-drying, distilled water was added to each of the freeze-dried product to be a concentration of gamma-globulin of 5 to 5.2% wt./vol., and the anticomplementary activity was measured according to the method of Kabat and Mayer, described in Experimental Immunochemistry, page 225, XII Ed. 1961, after having subjected the aqueous mixture to dialysis against the aqueous physiological saline solution to remove the amino acid contained therein from the consideration of the effect of the amino acid on the determination of the anticomplementary activity.

The results are shown in Table 1.

TABLE 1

| Additive (0.2 mol/liter) | Anticomplementary activity ($C'H_{50}$)* | |
|---|---|---|
| | Before freeze-drying | After freeze-drying |
| Not added | 12 | 47 |
| Glycine | 12 | 30 |
| L-Alanine | 12 | 44 |
| L-Arginine | 12 | 14 |
| L-Arginine hydrochloride | 12 | 14 |
| L-Lysine | 12 | 14 |
| L-Lysine hydrochloride | 12 | 14 |
| L-Ornithine hydrochloride | 12 | 32 |
| Sodium L-aspartate | 12 | 22 |
| Sodium L-glutamate | 12 | 26 |
| epsilon-aminocaproic acid | 12 | 23 |

Note:
*The figures indicate the amount of the complement inactivated by the different preparation of gamma-globulin expressed in percent of the complement added in the form of serum of a guinea-pig.

As is seen in the results of the present experiments shown in Table 1, L-arginine, L-lysine and their sodium salts showed a conspicuous effect on inhibiting the raise of the anticomplementary activity of the gamma-globulin to which one of them was added as compared with other amino acids. In addition, L-ornithine hydrochloride did not show any effect although L-ornithine belongs also to amino acid.

EXAMPLE 2

The similar experiment as in Example 1 was carried out on the four species of additives which showed conspicuous effectiveness in Example 1 concerning the relationship between their respective effectiveness and their respective amounts of addition. The results are shown in Table 2.

TABLE 2

|  |  | unit: % Amount added (mol/liter) |  |  |  |  |  |  |  |
|---|---|---|---|---|---|---|---|---|---|
| Additive |  | 0 | 0.05 | 0.10 | 0.15 | 0.20 | 0.30 | 0.40 | 0.50 |
| L-Arginine.HCl | before* | 12 | 12 | 12 | 12 | 12 | 12 | 12 | 12 |
|  | after** | 50 | 39 | 36 | 18 | 14 | 13 | —*** | — |
| L-Lysine.HCl | before | 12 | 12 | 12 | 12 | 12 | 12 | 12 | 12 |
|  | after | 49 | 47 | 33 | 19 | 14 | 13 | — | — |
| L-Arginine | before | 12 | 12 | 12 | 12 | 12 | 12 | 12 | 12 |
|  | after | 51 | 38 | 35 | 18 | 14 | 13 | — | — |
| L-Lysine | before | 12 | 12 | 12 | 12 | 12 | 12 | 12 | 12 |
|  | after | 50 | 48 | 34 | 19 | 14 | 13 | — | — |

Notes:
*before freeze-drying,
**after freeze-drying,
***The mixture could not be freeze-dried.

As is seen in Table 2, each of these amino acids and their salts could not exhibit the effectiveness of inhibiting the raise of the anticomplementary activity at a concentration lower than 0.1 mol/liter, and at a concentration higher than 0.4 mol/liter, it became a hindrance in carrying out the freeze-drying. That is, the optimum amount of addition of the additive was found to be in the range of 0.15 to 0.3 mol/liter.

EXAMPLE 3

Four kinds of the preparation of gamma-globulin for pharmaceutical use prepared and freeze-dried by the same procedures in Example 2, however, at a respective concentration of 0.2 mol/liter of amino acids and their salts were kept for one month and 2 weeks, respectively at temperatures of 4° C. and 37° C., respectively, to examine the change of their anticomplementary activity during such a period of storage.

The results of the examination revealed that the anticomplementary activity did not show any change from 14 ($C'H_{50}$) even after one month at 4° C., and after two weeks at 37° C. It has been thus known that gamma-globulin when added with one of these amino acids and their salts can be stored for a long period in a stabilized state concerning its anticomplementary activity.

EXAMPLE 4

Into 20 ml of an aqueous physiological saline solution, one gram of a gamma-globulin prepared by a method other than the method according to the present invention, not yet stabilized and showing its anticomplementary activity of 15 ($C'H_{50}$) was dissolved and L-arginine hydrochloride was added to the solution in an amount corresponding to 0.2 mol/liter of the solution. After adjusting the pH of the solution to 7.0 by 1 N aqueous solution of sodium hydroxide, the solution was sterilized by passing through a millipore filter of pore size of 0.45 micron and poured into vials to be freeze-dried. The thus prepared pharmaceutical preparation showed its anticomplementary activity of 15 ($C'H_{50}$) just after the freeze-drying and also after keeping for one month at a constant temperature of 4° C.

EXAMPLE 5

One gram of the Cohn's Fraction II was brought into suspension in 50 ml of an aqueous 10% solution of glucose, and after adjusting the pH of the suspension to 7.2 with 1 N aqueous solution of sodium hydroxide, one gram of Dextran 40 was added and the mixture was well shaken, and left stand for one hour. Then, it was centrifugated for 30 min at 10,000 rpm to separate the supernatant layer. One gram of Dextran 40 was added to the supernatant layer, and the same procedure as above was carried out. To the thus obtained supernatant layer, one gram of Dextran 40 was added, and the same procedure was repeated once. The thus obtained supernatant layer was cooled to 4° C., and 10 g of ammonium sulfate was added to the cooled supernatant layer, and after well stirred, the mixture was left stand for 2 hours and centrifugated for 30 min at 10,000 rpm to obtain the object, that is, the precipitate of gamma-globulin at a yield of 76%.

After dissolving the thus obtained precipitate into an aqueous physiological saline solution and subjecting the solution to dialysis against the aqueous physiological saline solution to remove ammonium sulfate, the concentration of gamma-globulin of the dialyzate was adjusted to 5% by weight, and its anticomplementary activity was measured by the above-mentioned method of Kabat and Mayer. The activity was 13%.

EXAMPLES 6 to 14

The same procedures were carried out as in Example 5 only changing the species of sugar and the pH of the solution of the raw material. The results of the thus carried out runs are shown in Table 3.

COMPARATIVE EXAMPLES 1 to 4

In these Comparative Examples, the same procedures were carried out as in Example 5, however, Cohn's Fraction II was dissolved into water, instead of dissolving into the solution of glucose in Example 5, the results being shown also in Table 3.

TABLE 3

| Example | Sugar | pH | Yield (%) | Anticomplementary activity ($C'H_{50}$) |
|---|---|---|---|---|
| 6 | glucose | 7.7 | 82 | 14 |
| 7 | glucose | 8.2 | 75 | 11 |

TABLE 3-continued

| Example | Sugar | pH | Yield (%) | Anticomplementary activity (C'H$_{50}$) |
|---|---|---|---|---|
| 8 | lactose | 7.7 | 93 | 13 |
| 9 | fructose | 7.7 | 74 | 15 |
| 10 | galactose | 7.7 | 79 | 5 |
| 11 | maltose | 7.7 | 76 | 11 |
| 12 | mannitol | 7.7 | 79 | 7 |
| 13 | xylitol | 7.7 | 79 | 11 |
| 14 | glycerol | 7.7 | 85 | 12 |
| Com. 1* | none | 7.2 | 80 | 25 |
| Com. 2 | none | 7.7 | 72 | 30 |
| Com. 3 | none | 8.2 | 63 | 28 |
| Com. 4 | none | 8.7 | 74 | 28 |

Note:
Com. means Comparative Example

EXAMPLE 15

Into 400 ml of aqueous 12% by weight solution of mannitol, 12 g of powdery Cohn's Fraction II (containing 10.3 g of globulin) were dissolved and after adjusting the pH of the solution to 7.9, 146 ml of an aqueous 30% by weight solution of Dextran 40 were added to the above-mentioned solution, and the mixture was stirred for 30 min. After 2 hours of standing still, the mixture was centrifuged for 20 min at 7,000 rpm, and the supernatant layer was cooled to 4° C., and 163 g of ammonium sulfate was slowly added to the cooled supernatant. After leaving the mixture still over a night, it was centrifuged again for 15 min at 7,000 rpm. The thus obtained precipitate was brought into suspension in 400 ml of an aqueous 40% by weight solution of ammonium sulfate, and after one hour of standing still, the aqueous suspension was centrifuged for 15 min at 7,000 rpm to obtain the object, gamma-globulin, at a yield of 82%, as a precipitate.

After dissolving this precipitate into about 100 ml of an aqueous physiological saline solution and then dialyzing the solution against the physiological solution for 24 hours, the concentration of gamma-globulin of the dialyzate was adjusted to be 5% by weight. Then, after adding 0.2 mol/liter equivalent of L-arginine hydrochloride and adjusting the pH of the mixture to 7.0, the mixture was centrifuged for 20 min at 7,000 rpm. The centrifugate was sterilized by passing through the millipore-filter of 0.45 micron, and then dividedly poured into vials at 20 ml to be freeze-dried. The anticomplementary activity of the thus obtained product was 12 (C'H$_{50}$), and according to the test result carried out by the method of inhibiting the aggregation of erythrocytes, the value of antibody of measles expressed by the highest times of dilution to cause the aggregation was 1024. These two values were respectively the same as those shown before freeze-drying.

EXAMPLE 16

Another freeze-dried product of the preparation according to the present invention was obtained by the same procedures as in Example 15, however, adding 0.2 mol/liter equivalent of L-lysine hydrochloride instead of L-arginine hydrochloride in Example 15. The anticomplementary activity and the value of antibody of measles of this preparation were 12 (C'H$_{50}$) and 1024 (times), respectively which were respectively the same as those before freeze-drying.

The thus prepared pharmaceutical preparation of gamma-globulin for use in intravenous administration according to the present invention is safely administrable intravenously as is verified by the results of the following acute toxicity test:

Acute toxicity test

Each of the three pharmaceutical preparations of gamma-globulin for use in intravenous administration, two of which were prepared in Examples 15 and 16, respectively and the remaining one of which was prepared following the procedures in Example 15, however, using L-arginine instead of its hydrochloride in Example 15 was dissolved into distilled water for injection at a concentration of 2.0 g/20 ml. Each of the thus prepared solution was injected into the groups of mice intra-caudal-venously at respective rates of 32, 40 and 50 ml/kg, one group of mice being composed of 5 aminals, and the state, behaviour and mortality, if any, of the treated mice and control were observed for 7 days.

No abnormal findings nor mortality were obtained by the above-mentioned careful observation.

In addition, the dose of the pharmaceutical preparation of gamma-globulin for use in intravenous administration according to the present invention depends on the age, the physical conditions, etc. of the subject, however, usually an amount of 1.6 to 6.0 g (1,000 to 2,500 mg as gamma-globulin) and 75 to 360 mg (50 to 150 mg as gamma-globulin) for an adult and a child, respectively, is used at a time.

What is claimed is:

1. A process for producing gamma-globulin suitable for use in intravenous administration and of an anticomplementary activity of lower than 20% (C'H$_{50}$ value) comprising, bringing Cohn's Fraction II for said gamma-globulin into suspension in an aqueous solution of a monosaccharide, disaccharide or sugar alcohol, adjusting the pH of said suspension to 7.0 to 9.0, adding dextran of an average molecular weight of 10,000 to 70,000 into said suspension to produce an aqueous 2 to 10% wt./vol. solution of dextran, and after removing the thus formed precipitate, adding ammonium sulfate to the mother liquor to precipitate said gamma-globulin.

* * * * *